(12) United States Patent
Fukaya et al.

(10) Patent No.: US 10,345,489 B2
(45) Date of Patent: Jul. 9, 2019

(54) ANTIREFLECTION FILM, OPTICAL ELEMENT AND OPHTHALMOLOGY APPARATUS

(71) Applicant: TOPCON CORPORATION, Tokyo (JP)

(72) Inventors: Hiroki Fukaya, Tokyo (JP); Kenichiro Miyazawa, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 118 days.

(21) Appl. No.: 15/249,706

(22) Filed: Aug. 29, 2016

(65) Prior Publication Data

US 2017/0090071 A1 Mar. 30, 2017

(30) Foreign Application Priority Data

Sep. 30, 2015 (JP) .................................. 2015-194538

(51) Int. Cl.
| | | |
|---|---|---|
| *G02B 1/115* | (2015.01) | |
| *G02B 5/28* | (2006.01) | |
| *A61B 3/10* | (2006.01) | |
| *C03C 17/34* | (2006.01) | |

(52) U.S. Cl.
CPC .......... *G02B 1/115* (2013.01); *C03C 17/3452* (2013.01); *G02B 5/285* (2013.01); *A61B 3/102* (2013.01); *C03C 2217/734* (2013.01)

(58) Field of Classification Search
CPC ..... G02B 1/115; G02B 5/282; C03C 17/3452; C03C 2217/734; A61B 3/102

USPC .......................................................... 359/589
See application file for complete search history.

(56) References Cited

U.S. PATENT DOCUMENTS

| | | | |
|---|---|---|---|
| 6,590,702 B1* | 7/2003 | Shirai .................... | G02B 1/115 |
| | | | 257/E21.029 |
| 2005/0019484 A1* | 1/2005 | Arfsten ................... | C03C 17/25 |
| | | | 427/162 |
| 2013/0271836 A1 | 10/2013 | Fukaya et al. | |
| 2015/0062531 A1* | 3/2015 | Buckland ............... | A61B 3/005 |
| | | | 351/206 |
| 2015/0132554 A1* | 5/2015 | Yamaguchi ............ | G02B 27/00 |
| | | | 428/213 |

FOREIGN PATENT DOCUMENTS

| | | |
|---|---|---|
| JP | H8-98812 A | 4/1996 |
| JP | 2006-47924 A | 2/2006 |
| JP | 2007-333806 A | 12/2007 |
| JP | 2008-225210 A | 9/2008 |
| JP | 2009-008901 A | 1/2009 |
| JP | 2013-156523 A | 8/2013 |

OTHER PUBLICATIONS

An Office Action; "Notification of Reasons for Refusal," issued by the Japanese Patent Office dated Jan. 8, 2019, which corresponds to Japanese Patent Application No. 2015-194538 and is related to U.S. Appl. No. 15/249,706; with English Translation.

* cited by examiner

*Primary Examiner* — Collin X Beatty
(74) *Attorney, Agent, or Firm* — Studebaker & Brackett PC

(57) ABSTRACT

An antireflection film is provided on a substrate. The antireflection film includes at least nine layers. An outermost layer of the nine layers is formed by $SiO_2$ or $MgF_2$.

18 Claims, 6 Drawing Sheets

ANTIREFLECTION FILM, OPTICAL ELEMENT AND OPHTHALMOLOGY APPARATUS

CROSS-REFERENCE TO RELATED APPLICATION

This application is based upon and claims the benefit of priority from Japanese Patent Application No. 2015-194538, filed on Sep. 30, 2015, the entire disclosure of which is incorporated herein by reference.

BACKGROUND

Technical Field

The present invention relates to an antireflection film that restrains reflection of light in a range from visible light to near-infrared light, an optical element including the antireflection film, and an ophthalmology apparatus including the optical element.

Description of Related Art

It is conventionally known that an antireflection film is provided on a surface of an optical element such as a lens to reduce reflection of incident light. As such an antireflection film, a technology that a layer of $MgF_2$ is laminated on the outermost side of the antireflection film is disclosed (see, for example, JP2009-8901A and JP2007-333806A).

However, an antireflection film described in JP2009-8901A or JP2007-333806A has a characteristic of low reflectivity in visible light of about 350 nm to 700 nm, but JP2009-8901 A and JP2007-333806 A do not disclose reflectivity in a wide band from a visible light range to a near-infrared range. In addition, in the antireflection film, a phenomenon that the incident light is attenuated may occur depending on a combination of film materials. There are possibilities that the phenomenon prevents the antireflection film from having sufficient antireflection effect and influences the productivity of the antireflection film and optical parts.

SUMMARY

The disclosure is made in view of the above circumstances and an object of the disclosure is to provide an antireflection film that has excellent antireflection effect in a wide range including the visible light range and the near-infrared range and has excellent productivity, an optical element including the antireflection film, and an ophthalmology apparatus including the optical element.

To accomplish the above object, an antireflection film according to one embodiment of the present invention is provided on a substrate and includes a laminate having at least nine layers. The outermost layer is formed by $SiO_2$ or $MgF_2$.

DETAILED DESCRIPTION

Embodiments of an antireflection film, an optical element including the antireflection film, and an ophthalmology apparatus including the optical element according to the disclosure will be described hereinafter with reference to the accompanying drawings.

Figure 1A:
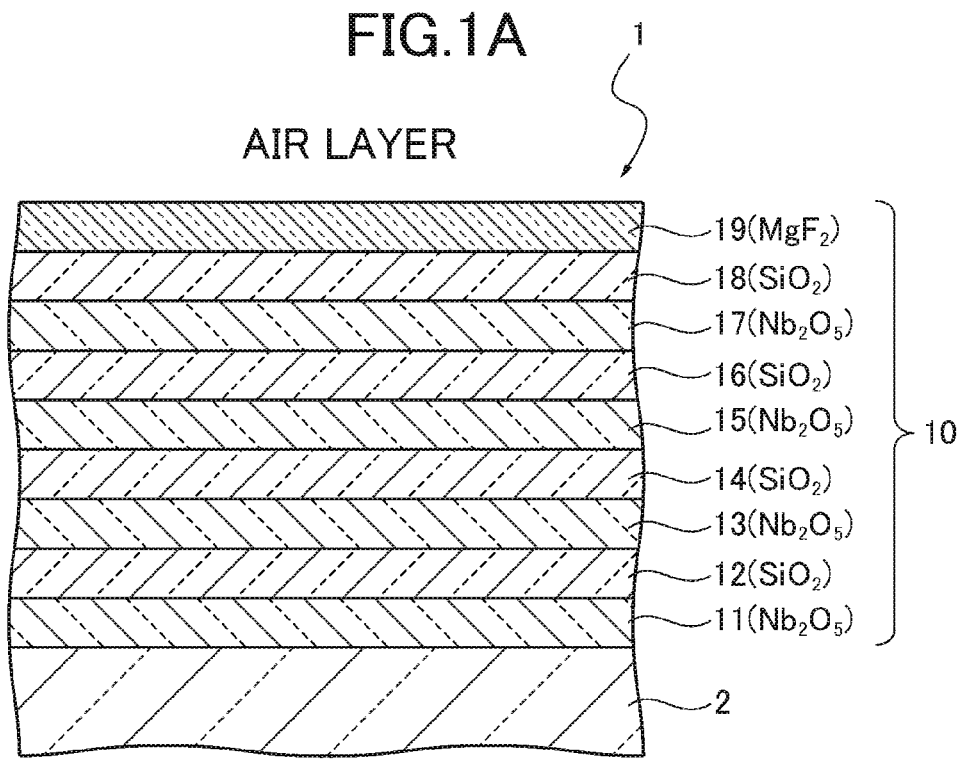
FIG. 1A is a sectional view of an optical element provided with an antireflection film according to Embodiment 1.
Figure 2:
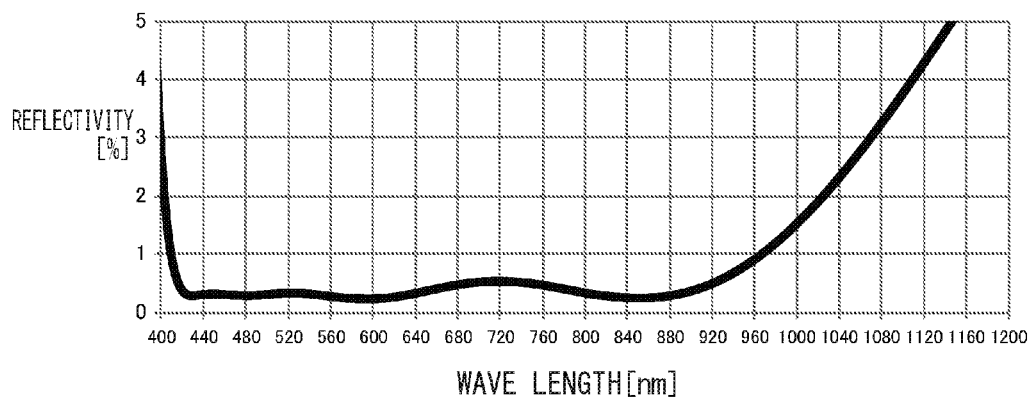
FIG. 2 is a graph showing an optical characteristic of the antireflection film according to Embodiment 1.

An optical element 1 including an antireflection film 10 according to Embodiment 1 is described with reference to FIGS. 1A and 2. FIG. 1A is a sectional view illustrating a schematic configuration of the optical element 1 including the antireflection film 10 according to Embodiment 1. FIG. 2 is a graph illustrating an optical characteristic of the antireflection film 10 according to Embodiment 1 and more specifically, is a reflectivity distribution map of the antireflection film against light in a visible range and a near-infrared range.

As shown in FIG. 1A, the optical element 1 according to Embodiment 1 is formed on a substrate 2 and includes the antireflection film 10 in which at least nine layers are laminated on the substrate 2.

The antireflection film 10 includes a first layer 11 of $Nb_2O_5$ (niobium pentoxide), a second layer 12 of $SiO_2$ (silicon dioxide), a third layer 13 of $Nb_2O_5$, a fourth layer 14 of $SiO_2$, a fifth layer 15 of $Nb_2O_5$, a sixth layer 16 of $SiO_2$, a seventh layer 17 of $Nb_2O_5$, an eighth layer 18 of $SiO_2$, and a ninth layer 19 of $MgF_2$ (magnesium difluoride) which are laminated in order from the substrate 2, as shown in FIG. 1A. An air layer is formed outside (opposite side to the substrate 2) the ninth layer 19. By forming each layer in this order, the antireflection film 10 can be used in a band ranging from the visible range (420 nm to 800 nm) to the near-infrared range (800 nm to 900 nm).

The antireflection film 10 of this embodiment includes a laminate. In Embodiment 1, the laminate includes a plurality of layers 11 to 18 of $Nb_2O_5$ and of $SiO_2$ arranged in order from the substrate 2 and the outermost layer 19 of $MgF_2$.

A vacuum evaporation method, an Ion-beam Assisted Deposition (IAD) film forming method, an ion plating film forming method, a spattering method, or the like may be used as a method of forming the antireflection film, without it being limited to the above.

As the substrate 2, a glass substrate ("TIH11" made by Ohara Co., Ltd) having a refractive index of 1.6 or more is used in Embodiment 1. Note that the antireflection film 10 in Embodiment 1 may be formed on other substrate having similar optical performance to "TIH11", without it being limited to "TIH11".

In a conventional antireflection film having a laminate of layers of $Nb_2O_5$ and layers of $MgF_2$ arranged in order from the substrate, there is a possibility that problems such as film formation failure occur, as a result, incident light is attenuated. In other words, a phenomenon that the incident light is absorbed may occur. In fact, the phenomenon occurs in around two times of frequencies per five times of film forming operations. This influences productivity of optical components.

The disclosure has been made by the inventors in consideration of the following circumstances. After the inventors of the disclosure tried to laminate layers of $SiO_2$, in order from the substrate, between the $Nb_2O_5$ layers and the $MgF_2$ layers of a laminate formed of the $Nb_2O_5$ layers and the $MgF_2$ layers, it has been found out that the film formation was efficiently accomplished and the occurrence of the phenomenon of attenuating the incident light could be reduced. In addition, it has been found out that excellent antireflection effects could be acquired throughout a wide band ranging from the visible range to the near-infrared range when forming the antireflection film with nine layers, although the antireflection film with eight layers could not acquire the excellent antireflection effects in the band ranging from the visible range (420 nm to 800 nm) to the near-infrared range (800 nm to 900 nm).

A layer configuration, a material name, a refractive index in d-line, and a physical film thickness of each layer of the antireflection film 10 in Embodiment 1 are shown in the following Table 1.

TABLE 1

| LAYER | MATERIAL | REFRACTIVE INDEX | PHYSICAL FILM THICKNESS (nm) |
|---|---|---|---|
| AIR LAYER | — | 1.00000 | — |
| NINTH LAYER | $MgF_2$ | 1.38531 | 94.1 |
| EIGHTH LAYER | $SiO_2$ | 1.45998 | 18.53 |
| SEVENTH LAYER | $Nb_2O_5$ | 2.39526 | 24.31 |
| SIXTH LAYER | $SiO_2$ | 1.45998 | 21.66 |
| FIFTH LAYER | $Nb_2O_5$ | 2.39526 | 83.3 |
| FOURTH LAYER | $SiO_2$ | 1.45998 | 7.75 |
| THIRD LAYER | $Nb_2O_5$ | 2.39526 | 41.82 |
| SECOND LAYER | $SiO_2$ | 1.45998 | 24.15 |
| FIRST LAYER | $Nb_2O_5$ | 2.39526 | 16.21 |
| SUBSTRATE | TIH11 | — | — |

As shown in Table 1 and FIG. 1A, the antireflection film 10 in Embodiment 1 includes a nine layer configuration in which four layers of $Nb_2O_5$ each having a high refractive index of 2.3 or more and four layers of $SiO_2$ each having a low refractive index of 1.5 or less are laminated on the substrate 2 in order from the substrate 2, and a $MgF_2$ layer is laminated at the outermost side of the eight layers which is farthest from the substrate 2.

The configuration of the antireflection film 10 formed by the nine layers makes it possible to acquire excellent antireflection performance in the visible range and the near-infrared range. The arrangement of the eighth layer 18 of $SiO_2$ between the seventh layer 17 of $Nb_2O_5$ and the ninth layer 19 of $MgF_2$ makes it possible to efficiently execute the film formation and restrain the attenuation in the visible range and the near-infrared range, that is to say, restrain the absorption of the incident light. Accordingly, the quality and the productivity of the antireflection film 10 and the optical element 1 can be improved.

Note that tantalum (Ta), titanium (Ti), zirconium (Zr) etc. can be used, instead of niobium (Nb), as the high refractive material. More specifically, even other than the $Nb_2O_5$ as the high refractive material, tantalum oxide ($Ta_2O_5$), titanium oxide ($TiO_2$), zirconium oxide ($ZrO_2$) etc. can be used.

In Embodiment 1, as film formation procedure, the first layer 11 to the eighth layer 18 of the $Nb_2O_5$ layers and the $SiO_2$ layers are formed by the IAD film forming method and the outermost ninth layer of $MgF_2$ is formed by the vacuum evaporation method. With this film formation procedure, a lower reflectivity in the band ranging from the visible range to the near-infrared range can be realized. Because chemical and physical integrity of each layer is increased, it is possible to further enhance stability of the film formation, and improve the quality and the productivity of the antireflection film 10 and the optical element 1.

Here, all the layers may be formed by the IAD film forming method or all the layers may be formed by the vacuum evaporation method, without being limited to the film formation procedure as described above. The film formation can be executed by use of an ion plating film forming method, various spattering methods, or the like, other than the IAD film forming method and the vacuum evaporation method, or a combination of their film formation methods.

An optical characteristic (reflectivity map) of the optical element 1 including the antireflection film 10 configured as described above is shown in FIG. 2. As is clear from FIG. 2, in the antireflection film 10 in Embodiment 1, it is possible to realize a low reflectivity of 0.5 or less in the band ranging from the visible range (420 nm to 800 nm) to the near-infrared range (800 nm to 900 nm).

Figure 1B:
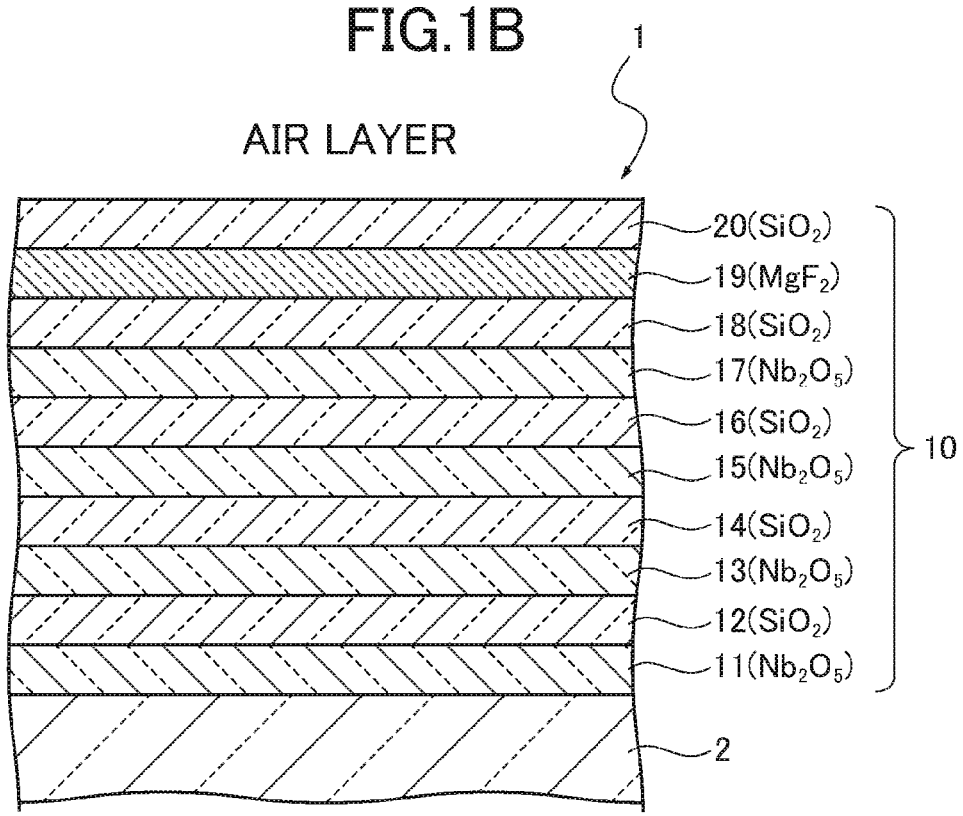
FIG. 1B is a sectional view of an optical element provided with an antireflection film according to Embodiment 2.

Next, an optical element provided with an antireflection film according to Embodiment 2 is described. As shown in FIG. 1B, the optical element according to Embodiment 2 has the same basic configuration as that of the optical element 1 in Embodiment 1 shown in FIG. 1A. However, the antireflection film 10 according to Embodiment 2 further includes a tenth layer 20 of $SiO_2$ laminated on an outer side of the antireflection film according to Embodiment 1 so as to provide an antifouling layer on the tenth layer 20 outside the ninth layer 19 of the antireflection film 10. The antireflection film according to Embodiment 2 has therefore a ten layer configuration.

A layer configuration and a material name, a refractive index in d-line, and a physical film thickness of each layer of the antireflection film in Embodiment 2 are shown in the following Table 2. In Embodiment 2, by laminating layers of materials as in the following Table 2 on the glass substrate "TIH11", the antireflection film that can be used in the band ranging from the visible range (to the near-infrared range) is formed.

TABLE 2

| LAYER | MATERIAL | REFRACTIVE INDEX | PHYSICAL FILM THICKNESS (nm) |
|---|---|---|---|
| AIR LAYER | — | 1.00000 | — |
| TENTH LAYER | $SiO_2$ | 1.45998 | 12.63 |
| NINTH LAYER | $MgF_2$ | 1.38531 | 78.51 |
| EIGHTH LAYER | $SiO_2$ | 1.45998 | 18.53 |
| SEVENTH LAYER | $Nb_2O_5$ | 2.39526 | 24.55 |
| SIXTH LAYER | $SiO_2$ | 1.45998 | 21.46 |
| FIFTH LAYER | $Nb_2O_5$ | 2.39526 | 83.31 |
| FOURTH LAYER | $SiO_2$ | 1.45998 | 7.99 |

TABLE 2-continued

| LAYER | MATERIAL | REFRACTIVE INDEX | PHYSICAL FILM THICKNESS (nm) |
|---|---|---|---|
| THIRD LAYER | $Nb_2O_5$ | 2.39526 | 41.6 |
| SECOND LAYER | $SiO_2$ | 1.45998 | 24.33 |
| FIRST LAYER | $Nb_2O_5$ | 2.39526 | 16.07 |
| SUBSTRATE | TIH11 | — | — |

The antifouling layer is provided on a surface of an object lens etc. to prevent fingerprint or dirt from adhering on the surface of the object lens etc. In Embodiment 2, the antifouling layer is laminated on an outer surface of the tenth layer 20 of $SiO_2$ outside the ninth layer 19 of $MgF_2$ of the antireflection film. As a material and a film forming method of the antifouling layer, the material and the film forming method disclosed in JP2013-156523A may be used, but other known materials and film forming methods can be used, without being limited to the above.

As in Embodiment 2, by disposing the tenth layer 20 of $SiO_2$ between the ninth layer of $MgF_2$ and the antifouling layer, it is possible to realize excellent antireflection effect in the band ranging from the visible range (420 nm to 800 nm) to the near-infrared range (800 nm to 900 nm), without the antireflection effect of the antireflection film being obstructed by the antifouling layer.

Figure 3:
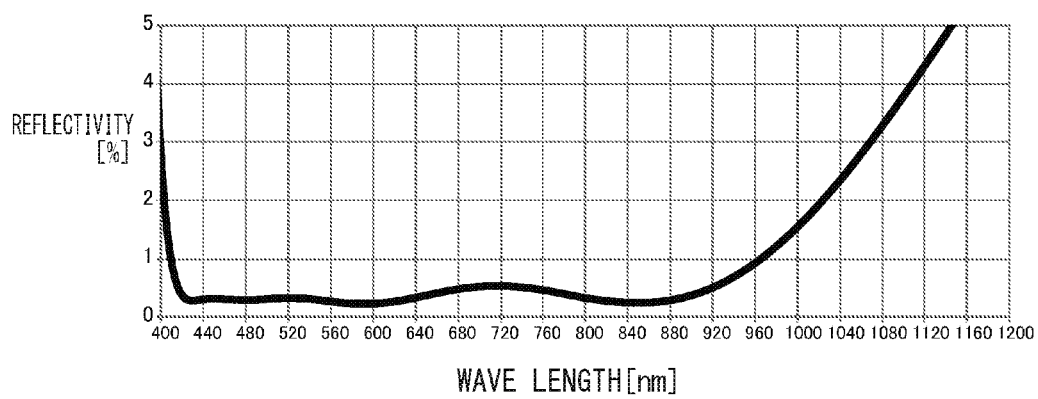
FIG. 3 is a graph showing an optical characteristic of the antireflection film according to Embodiment 2.

An optical characteristic (reflectivity distribution map) of the antireflection film in Embodiment 2 is illustrated in FIG. 3. As can be understood from FIG. 3, in the antireflection film in Embodiment 2, a low reflectivity of 0.5% or less can be realized in the band of the visible range (420 nm to 800 nm) and the near-infrared range (800 nm to 900 nm).

Next, an optical element provided with an antireflection film according to Embodiment 3 is described. The optical element 1 in Embodiment 3 uses, instead of the substrate "TIH11", a substrate 2, "BAL35" (glass substrate made by Ohara Co., Ltd) having a reflectivity lower than that of the substrate "TIH11". The optical element has the same basic configuration, that is, the antireflection film of the nine layer structure, as the optical element in Embodiment 1 shown in FIG. 1A, except that a physical thickness of each layer is changed. Even in this case, the substrate 2 is not limited to the "BAL35", but other substrates, for example, a substrate of glass material having an optical characteristic similar to that of the BAL35 substrate may be used, and the antireflection film in Embodiment 3 can be applied to the other substrates.

A layer configuration and a material name, a refractive index in d-line, and a physical film thickness of each layer of the antireflection film in Embodiment 3 are shown in the following Table 3. In Embodiment 3, by laminating layers of materials as in the following Table 3 on the glass substrate "BAL35", the antireflection film that can be used for the band ranging from the visible range (420 nm to 800 nm) to the near-infrared range (800 nm to 900 nm) is formed.

TABLE 3

| LAYER | MATERIAL | REFRACTIVE INDEX | PHYSICAL FILM THICKNESS (nm) |
|---|---|---|---|
| AIR LAYER | — | 1.00000 | — |
| NINTH LAYER | $MgF_2$ | 1.38559 | 98.66 |
| EIGHTH LAYER | $SiO_2$ | 1.46037 | 11.67 |
| SEVENTH LAYER | $Nb_2O_5$ | 2.39945 | 24.69 |
| SIXTH LAYER | $SiO_2$ | 1.46037 | 20.11 |
| FIFTH LAYER | $Nb_2O_5$ | 2.39945 | 87.39 |
| FOURTH LAYER | $SiO_2$ | 1.46037 | 12.22 |

TABLE 3-continued

| LAYER | MATERIAL | REFRACTIVE INDEX | PHYSICAL FILM THICKNESS (nm) |
|---|---|---|---|
| THIRD LAYER | $Nb_2O_5$ | 2.39945 | 34.56 |
| SECOND LAYER | $SiO_2$ | 1.46037 | 36.78 |
| FIRST LAYER | $Nb_2O_5$ | 2.39945 | 12.79 |
| SUBSTRATE | BAL35 | — | — |

Figure 4:
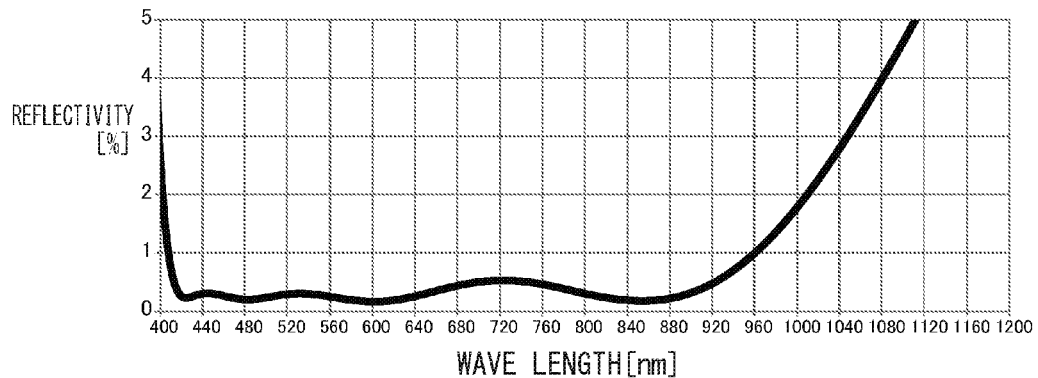
FIG. 4 is a graph showing an optical characteristic of the antireflection film according to Embodiment 3.

An optical characteristic (reflectivity map) of the antireflection film in Embodiment 3 is illustrated in FIG. 4. As can be understood from FIG. 4, in the antireflection film in Embodiment 3, a low reflectivity of 0.5% or less can be realized in the band of the visible range (420 nm to 800 nm) to the near-infrared range (800 nm to 900 nm).

Figure 1C:
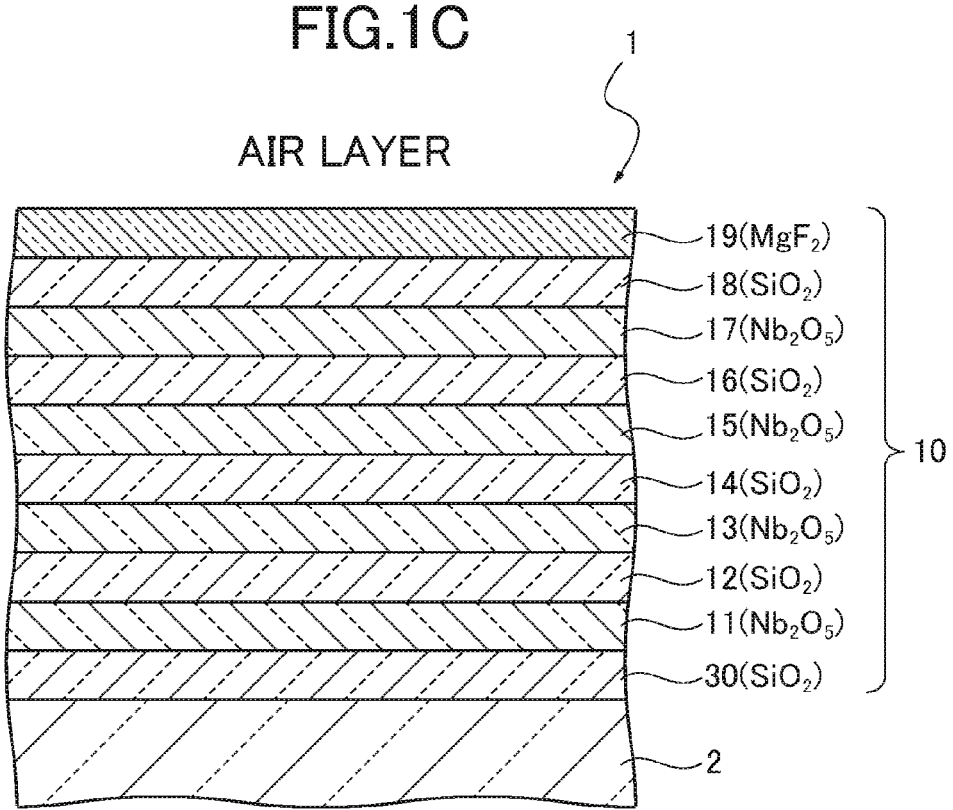
FIG. 1C is a sectional view of an optical element provided with an antireflection film according to Embodiment 4.

Next, an optical element provided with an antireflection film in Embodiment 4 is described. As shown in FIG. 1C, the optical element in Embodiment 4 has the same basic configuration as that of Embodiment 1 shown in FIG. 1A, but the antireflection film is formed to have a ten layer structure by disposing an additional layer 30 of $SiO_2$ between the substrate 2 and the layer 11 of $Nb_2O_5$.

A layer configuration and a material name, a refractive index in d-line, and a physical film thickness of each layer of the antireflection film in Embodiment 4 are shown in the following Table 4. In Embodiment 4, by laminating layers of materials as shown in the following Table 4 on the glass substrate "TIH11", the antireflection film that can be used for a band from the visible range (420 nm to 800 nm) to a near-infrared range of 1,000 nm to 1,100 nm is formed.

TABLE 4

| LAYER | MATERIAL | REFRACTIVE INDEX | PHYSICAL FILM THICKNESS (nm) |
|---|---|---|---|
| AIR LAYER | — | 1.00000 | — |
| TENTH LAYER | $MgF_2$ | 1.37726 | 101.18 |
| NINTH LAYER | $SiO_2$ | 1.45441 | 14.11 |
| EIGHTH LAYER | $Nb_2O_5$ | 2.30466 | 24.27 |
| SEVENTH LAYER | $SiO_2$ | 1.45441 | 25.28 |
| SIXTH LAYER | $Nb_2O_5$ | 2.30466 | 150.84 |
| FIFTH LAYER | $SiO_2$ | 1.45441 | 24.34 |
| FOURTH LAYER | $Nb_2O_5$ | 2.30466 | 29.56 |
| THIRD LAYER | $SiO_2$ | 1.45441 | 51.51 |
| SECOND LAYER | $Nb_2O_5$ | 2.30466 | 17.9 |
| FIRST LAYER | $SiO_2$ | 1.45441 | 31.86 |
| SUBSTRATE | TIH11 | — | — |

Figure 5:
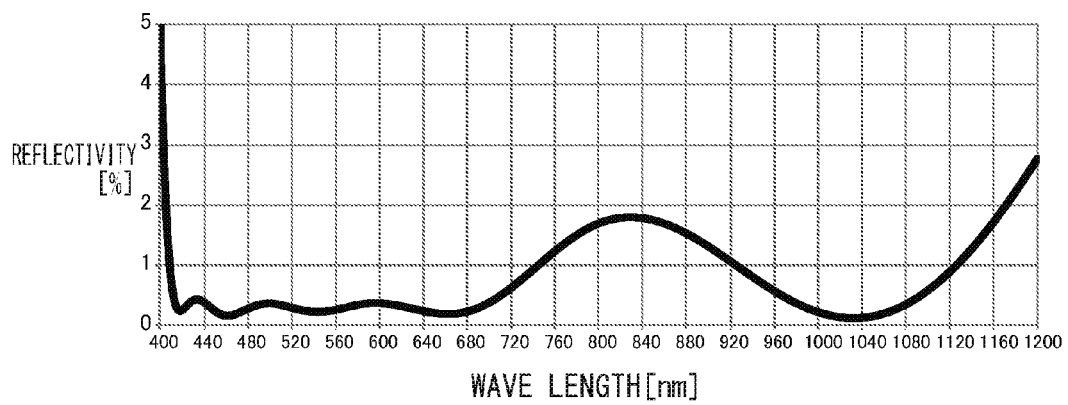
FIG. 5 is a graph showing an optical characteristic of the antireflection film according to Embodiment 4.

An optical characteristic (reflectivity map) of the antireflection film in Embodiment 4 is illustrated in FIG. 5. As can be understood from FIG. 5, in the antireflection film in Embodiment 4, a low reflectivity of 0.5% or less can be realized in bands of a visible range (420 nm to 720 nm) and the near-infrared range (1,000 nm to 1,100 nm).

Figure 1D:
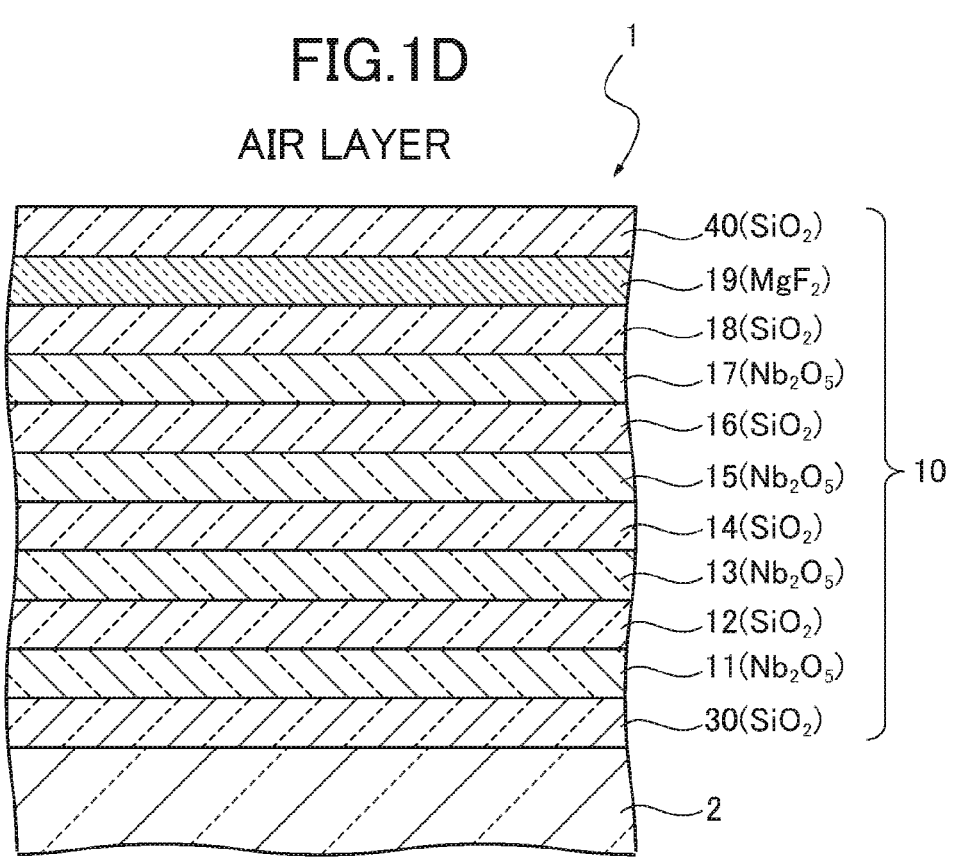
FIG. 1D is a sectional view of an optical element provided with an antireflection film according to Embodiment 5.

Next, an optical element provided with an antireflection film in Embodiment 5 is described. As shown in FIG. 1D, the optical element in Embodiment 5 has the same basic configuration as that of Embodiment 1 shown in FIG. 1A, but the antireflection film is formed to have an eleventh layer structure by further disposing a layer 40 of $SiO_2$ on the outer side of the outermost layer 19 of $MgF_2$ so as to provide an antifouling layer as an exterior coating of the antireflection film.

A layer configuration and a material name, a refractive index in d-line, and a physical film thickness of each layer of the antireflection film in Embodiment 5 are shown in the following Table 5. In Embodiment 5, by laminating layers of materials as shown in the following Table 5 on the glass substrate "TIH11", the antireflection film that can be used for the band from the visible range to the near-infrared range of 1,000 nm to 1,100 nm is formed.

TABLE 5

| LAYER | MATERIAL | REFRACTIVE INDEX | PHYSICAL FILM THICKNESS (nm) |
|---|---|---|---|
| AIR LAYER | — | 1.00000 | — |
| ELEVENTH LAYER | $SiO_2$ | 1.45441 | 11.68 |
| TENTH LAYER | $MgF_2$ | 1.37726 | 86.73 |
| NINTH LAYER | $SiO_2$ | 1.45441 | 14.11 |
| EIGHTH LAYER | $Nb_2O_5$ | 2.30466 | 24.42 |
| SEVENTH LAYER | $SiO_2$ | 1.45441 | 25.2 |
| SIXTH LAYER | $Nb_2O_5$ | 2.30466 | 150.77 |
| FIFTH LAYER | $SiO_2$ | 1.45441 | 24.37 |
| FOURTH LAYER | $Nb_2O_5$ | 2.30466 | 29.53 |
| THIRD LAYER | $SiO_2$ | 1.45441 | 51.19 |
| SECOND LAYER | $Nb_2O_5$ | 2.30466 | 17.92 |
| FIRST LAYER | $SiO_2$ | 1.45441 | 31.25 |
| SUBSTRATE | TIH11 | — | — |

Figure 6:
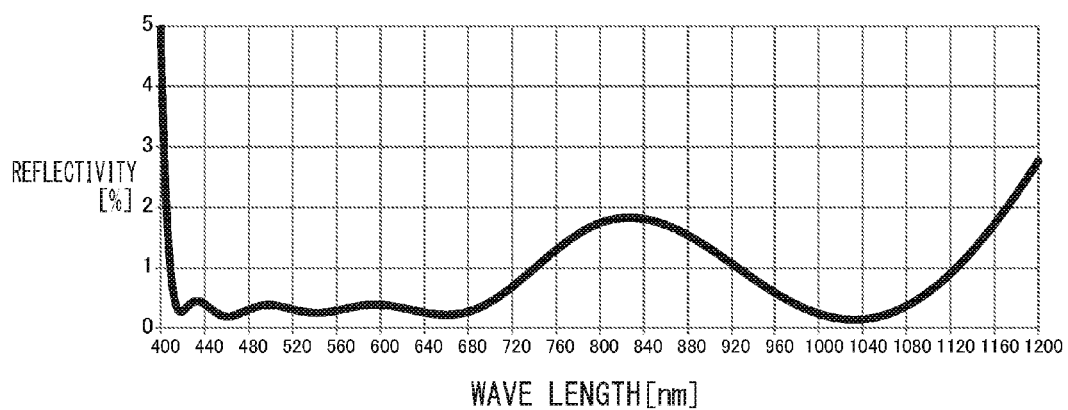
FIG. 6 is a graph showing an optical characteristic of the antireflection film according to Embodiment 5.

An optical characteristic (reflectivity map) of the antireflection film in Embodiment 5 is illustrated in FIG. 6. As can be understood from FIG. 6, in the antireflection film in Embodiment 5, a low reflectivity of 0.5% or less can be realized in bands of the visible range (420 nm to 720 nm) and the near-infrared range (1,000 nm to 1,100 nm).

Next, an optical element provided with an antireflection film according to Embodiment 6 is described. The optical element in Embodiment 6 has the same basic configuration, that is, the nine layer structure, as the optical element in Embodiment 3, except that a physical thickness of each layer is changed.

A layer configuration and a material name, a refractive index in d-line, and a physical film thickness of each layer of the antireflection film in Embodiment 6 are shown in the following Table 6. In Embodiment 6, by laminating layers of materials as shown in the following Table 6 on the glass substrate "BAL35", the antireflection film that can be used for the band from the visible range to the near-infrared range of 1,000 nm to 1,100 nm is formed.

TABLE 6

| LAYER | MATERIAL | REFRACTIVE INDEX | PHYSICAL FILM THICKNESS (nm) |
|---|---|---|---|
| AIR LAYER | — | 1.00000 | — |
| NINTH LAYER | $MgF_2$ | 1.37672 | 102.65 |
| EIGHTH LAYER | $SiO_2$ | 1.45422 | 11.83 |
| SEVENTH LAYER | $Nb_2O_5$ | 2.30113 | 24.41 |
| SIXTH LAYER | $SiO_2$ | 1.45422 | 25.03 |
| FIFTH LAYER | $Nb_2O_5$ | 2.30113 | 145.89 |
| FOURTH LAYER | $SiO_2$ | 1.45422 | 21.63 |
| THIRD LAYER | $Nb_2O_5$ | 2.30113 | 24.97 |
| SECOND LAYER | $SiO_2$ | 1.45422 | 40.76 |
| FIRST LAYER | $Nb_2O_5$ | 2.30113 | 7.11 |
| SUBSTRATE | BAL35 | — | — |

Figure 7:
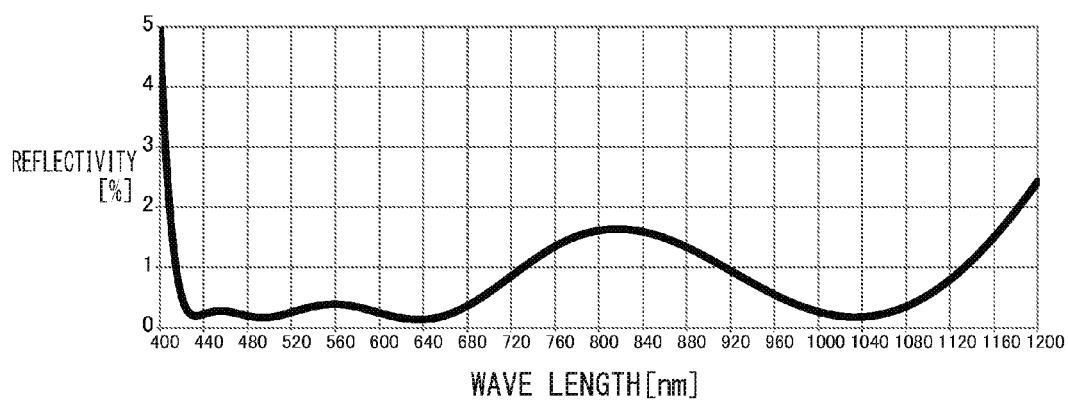
FIG. 7 is a graph showing an optical characteristic of the antireflection film according to Embodiment 6.

An optical characteristic (reflectivity map) of the antireflection film in Embodiment 6 is illustrated in FIG. 7. As can be understood from FIG. 7, in the antireflection film in Embodiment 6, a low reflectivity of 0.5% or less can be realized in bands of the visible range (420 nm to 720 nm) and the near-infrared range (1,000 nm to 1,100 nm).

Figure 8:
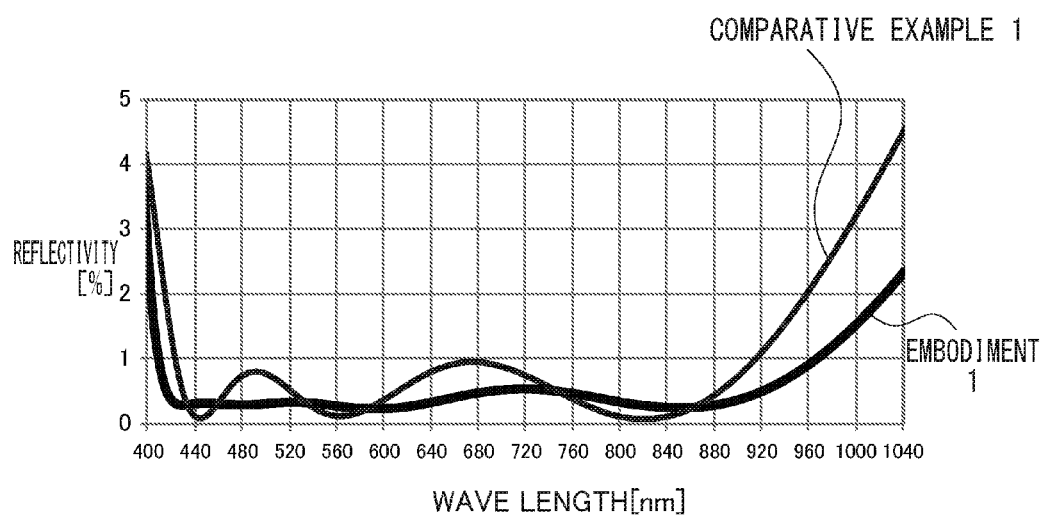
FIG. 8 is a graph comparing an optical characteristic according to Comparative Example 1 with the optical characteristic of the antireflection film according to Embodiment 1.

As Comparative Example 1 to Embodiment 1, an optical element including an antireflection film having eight layers was prepared. More specifically, the optical element of Comparative Example 1 was prepared by depositing on the glass substrate, "TIH11" the eight layers having the same configuration as the second layer 12 to the ninth layer 19 in Embodiment 1 shown in FIG. 1A, without providing the first layer 11 of $Nb_2O_5$ which is closest to the substrate 2. FIG. 8 illustrates a graph comparing an optical characteristic (reflectivity map) of the antireflection film in Comparative Example 1 with the optical characteristic (reflectivity map) of the antireflection film in Embodiment 1, in the band from the visible range to the near-infrared range. In FIG. 8, a thin line represents the optical characteristic of the antireflection film in Comparative Example 1 and a thick line represents the optical characteristic of the antireflection film in Embodiment 1.

As can be understood from FIG. 8, it is determined that the antireflection film of the nine layers in Embodiment 1, in which the first layer of 11 of $Nb_2O_5$ is provided, has excellent antireflection effect in the band from the visible range to the near-infrared range, as compared to the antireflection film of the eight layers in Comparative Example 1, in which the first layer of 11 of $Nb_2O_5$ is not provided.

Figure 9:
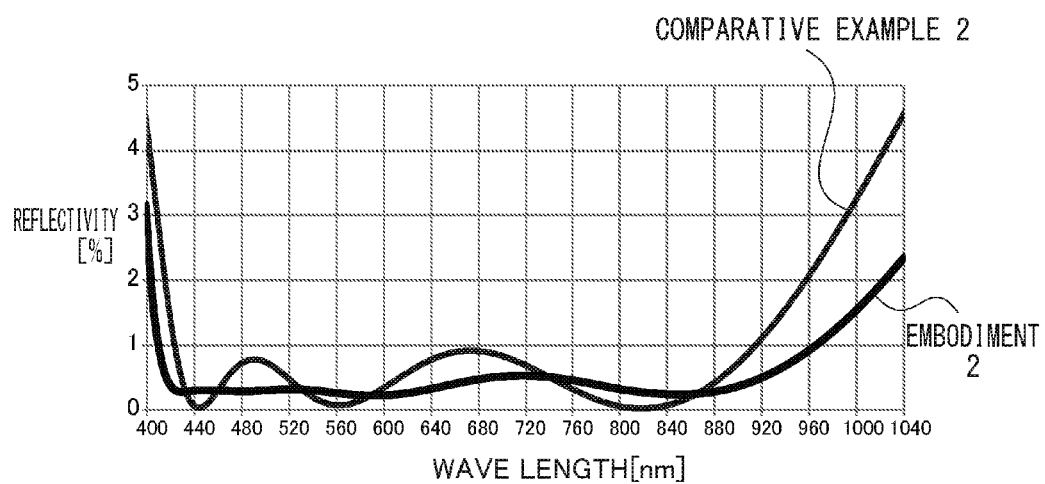
FIG. 9 is a graph comparing an optical characteristic according to Comparative Example 2 with the optical characteristic of the antireflection film according to Embodiment 2.

As Comparative Example 2 to Embodiment 2, an antireflection film having nine layers was prepared, without providing the first layer 11 of $Nb_2O_5$ which is closest to the substrate 2 in the antireflection film in Embodiment 2 shown in FIG. 1B. That is to say, the antireflection film has eight layers from the substrate 2 to the layer 19 of $MgF_2$. FIG. 9 illustrates a graph comparing an optical characteristic (reflectivity map) of the antireflection film in Comparative Example 2 with the optical characteristic (reflectivity map) of the antireflection film in Embodiment 2, in the band from the visible range to the near-infrared range. In FIG. 9, a thin line represents the optical characteristic of the antireflection film in Comparative Example 2 and a thick line represents the optical characteristic of the antireflection film in Embodiment 2.

As can be understood from FIG. 9, it is determined that the antireflection film of the ten layers (i.e., including nine layers from the substrate 2 to the ninth layer 19) in Embodiment 2, in which the first layer of 11 of $Nb_2O_5$ is provided, has excellent antireflection effect in the band from the visible range to the near-infrared range, as compared to the antireflection film in Comparative Example 2, in which the first layer of 11 of $Nb_2O_5$ is not provided to have eight layers from the substrate 2 to the layer 19 of $MgF_2$.

As other Comparative Examples, an optical element was prepared by forming an antireflection film without providing a layer of $SiO_2$ between a layer of $MgF_2$ and a layer of $Nb_2O_5$ in the layer configuration of the antireflection film of each of the optical elements in Embodiments 1 to 6. In the optical element of each of Comparative Examples, the phenomenon that incident light is absorbed occurred in around two times of frequencies per five times of film forming operations. On the contrary, the phenomenon did not occur in the optical element of each of Embodiments 1 to 6, in which the layer of $SiO_2$ is provided.

As a result, the antireflection film and the optical element including the antireflection film in each of Embodiments 1 to 6 can have excellent antireflection effect in the wide band from the visible range to the near-infrared range. In addition, the phenomenon that the incident light is absorbed in the film forming operations is suppressed. It is therefore possible to enhance the quality of the antireflection film and the optical element, maintain a uniform quality of products, and improve the productivity thereof. Furthermore, the antireflection film 10 and the optical element 1 in Embodiment 1 can be suitably used for an ophthalmology apparatus executing diagnosis, inspection etc. of eyes by using visible light or near-infrared light, in particular, an optical coherence tomography apparatus etc. such as a fundus inspection apparatus or a three-dimensional fundus image photographing apparatus.

Here, the antireflection film in each of Embodiments as described above has the nine to eleventh layer structure. As other embodiment, it is possible to form an antireflection film having a laminate structure of about twenty layers by increasing repeated layers of high refractive index materials ($Nb_2O_5$ etc.) and low refractive index materials ($SiO_2$ etc.) laminated on the substrate and laminating a layer of $MgF_2$ on an outside surface of the repeated layers. In such an antireflection film, not only excellent antireflection effect in the visible range and the near-infrared range can be obtained, but also optical image noise can be reduced. Consequently, the antireflection film can be suitably applied to a lens installed in the ophthalmology apparatus such as the optical coherence tomography apparatus etc.

Figure 10A:
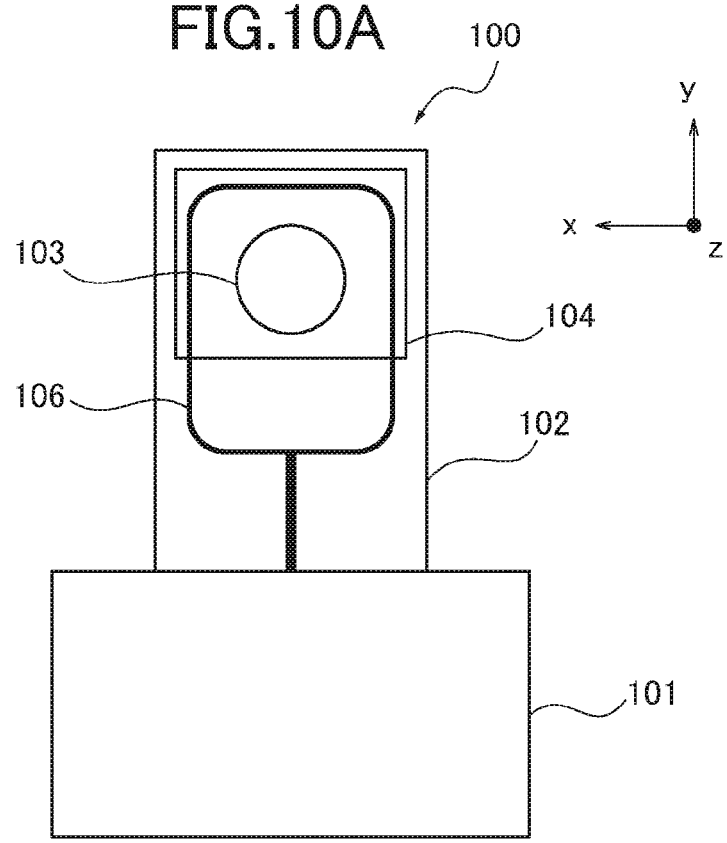
FIG. 10A is a front view of an ophthalmology apparatus according to Embodiment 7.
Figure 10B:
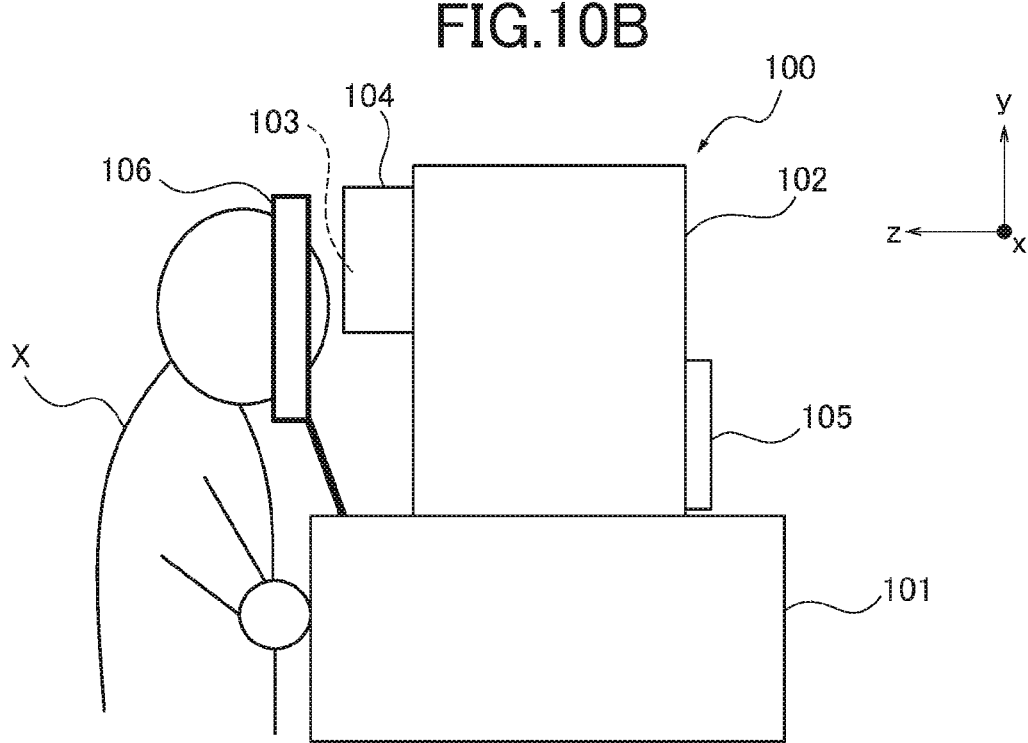
FIG. 10B is a side view of the ophthalmology apparatus according to Embodiment 7.

One embodiment of the ophthalmology apparatus provided with the optical element including the antireflection film of any of Embodiments 1 to 6, as Embodiment 7 is described hereinafter with reference to FIGS. 10A and 10B. FIGS. 10A and 10B are a front view and a side view of the optical coherence tomography apparatus 100 of Embodiment 7 as the ophthalmology apparatus, respectively.

As illustrated in FIGS. 10A and 10B, the optical coherence tomography apparatus 100 of Embodiment 7 includes a base 101 and an apparatus body 102. The apparatus body 102 has a lens housing 104 in which an optical system having an object lens 103 etc. is housed and a display 105 such as a liquid crystal display etc. displaying an operation screen, a measurement result and so on. The base 101 has in an inside portion thereof a control system controlling operation of the apparatus body 102, a drive system and so on and in an outside portion thereof a face receiver 106 having a jaw receiver and a forehead support, etc., to fix a position of a face (subject eye) of a subject (patient) X. The optical element provided with the antireflection film of any of Embodiments 1 to 6 is applied to the object lens 103 of the optical system. Note that the ophthalmology apparatus can be used for an optical coherence tomography apparatus having other configuration or an ophthalmology apparatus such as a fundus camera etc., without being limited to the optical coherence tomography apparatus 100 of Embodiment 7.

By applying the optical element provided with the antireflection film of any of Embodiments 1 to 6 to the object lens 103, in the optical coherence tomography apparatus 100 of Embodiment 7, a low reflectivity of 0.5% or less can be realized in the band of the visible range and the near-infrared range of 800 nm to 900 nm and in the band of the visible range and the near-infrared range of 1,000 nm to 1,100 nm. It is possible to improve the optical performance or the productivity of the ophthalmology apparatus such as the optical coherence tomography apparatus 100 by the excellent antireflection effect as described above.

According to the disclosure, by the above-described antireflection film having the configuration as described above, it is possible to provide an antireflection film having excellent antireflection effect throughout a wide band from a visible range to a near-infrared range. In addition, it is possible to enhance quality of the antireflection film in forming the film and productivity thereof. By having the antireflection film, it is possible to provide an optical element and an ophthalmology apparatus including the optical element, and enhance the productivity of the optical element and the ophthalmology apparatus.

In addition, the antireflection film according to the disclosure can be suitably applied to an optical element to allow visible light or near-infrared light to be incident and an ophthalmology apparatus executing inspection of eyes etc. with the visible light or near-infrared light.

The above-described antireflection film should have at least nine layers, and can form in ten layers depending on intended purposes or models of apparatuses to be used. For example, an antireflection film is configured to have a layer of $MgF_2$ as the outermost layer and at least four sets of layers including high refractive index materials ($Nb_2O_5$ etc.) having refractive indexes more than predetermined values and layers including low refractive index materials ($SiO_2$ etc.) having refractive indexes lower than that of the high refractive index materials, arranged in order from a substrate to an inner side of the outermost layer of $MgF_2$. In case where the antireflection fil has more than ten layers, it can be realized by setting sets of 5 layers or more or adding layers of low refractive index materials ($SiO_2$ etc.) on a substrate side.

Here, in the specification, "high refractive index material" means a material having a refractive index equal to or more than a predetermined value (for example, a refractive index in d-line is 1.5 or more, but without being limited to this), and "low refractive index material" means a material having a refractive index less than the predetermined value (for example, a refractive index in the d-line is less than 1.5, but without being limited to this).

The above-described antireflection film further preferably has a layer of $SiO_2$ on a side of the layer of $MgF_2$ opposite to the substrate so as to provide a film having other function such as an antifouling film on an outer layer. With the configuration, even if the antifouling film is provided, it is possible to restrain optical performance of the antireflection film from being reduced and realize excellent antireflection effect.

The antireflection film preferably realizes a low reflectivity of 1.0% or less, preferably 0.5% or less can be realized in the band of the visible range and the near-infrared range (800 nm to 900 nm). By satisfying this condition, the antireflection film can be suitably applied to a lens of an ophthalmology apparatus such as a three-dimensional fundus image photographing apparatus employing light interference measurement such as an SD-OCT using a low coherence light source close to a light-emitting wavelength of 840 nm.

The antireflection film preferably realizes a low reflectivity of 1.0% or less, preferably, 0.5% or less can be realized in the band of the visible range and the near-infrared range (1,000 nm to 1,100 nm). By satisfying this condition, the antireflection film can be suitably applied to a lens of an ophthalmology apparatus such as a three-dimensional fundus image photographing apparatus employing light interference measurement such as an SS-OCT using a wavelength sweeping light source close to a light-emitting wavelength of 1 μm.

Moreover, by providing the antireflection film as described above, the optical element and the ophthalmology apparatus can have excellent antireflection effect in the wide band from the visible range to the near-infrared range. As a result, the productivity of the optical element and the ophthalmology apparatus can be enhanced.

Although the several embodiments of the present invention have been described, it should be noted that the present invention is not limited to these embodiments, various modifications and changes can be made to the embodiments by those skilled in the art as long as such modifications and changes are within the scope of the present invention as defined by the Claims.

What is claimed is:

1. An antireflection film provided on a substrate, the antireflection film comprising:
   as viewed from the substrate:
   a first layer made of $Nb_2O_5$ of which a refractive index is 2.39526 and of which a physical film thickness is 16.21 nm,
   a second layer made of $SiO_2$ of which a refractive index is 1.45998 and of which a physical film thickness is 24.15 nm,
   a third layer made of $Nb_2O_5$ of which a refractive index is 2.39526 and of which a physical film thickness is 41.82 nm,
   a fourth layer made of $SiO_2$ of which a refractive index is 1.45998 and of which a physical film thickness is 7.75 nm,
   a fifth layer made of $Nb_2O_5$ of which refractive index is 2.39526 and of which a physical film thickness is 83.3 nm,
   a sixth layer made of $SiO_2$ of which a refractive index is 1.45998 and of which a physical film thickness is 21.66 nm,
   a seventh layer made of $Nb_2O_5$ of which a refractive index is 2.39526 and of which a physical film thickness is 24.31 nm,
   an eighth layer made of $SiO_2$ of which a refractive index is 1.45998 and of which a physical film thickness is 18.53 nm,
   a ninth layer made of $MgF_2$ of which a refractive index is 1.38531 and of which a physical film thickness is 94.1 nm, and
   an air layer, wherein the substrate is made of glass.

2. An optical element comprising the antireflection film claimed in claim 1.

3. An ophthalmology apparatus comprising the optical element claimed in claim 2.

4. An antireflection film provided on a substrate, the antireflection film comprising:
   as viewed from the substrate:
   a first layer made of $Nb_2O_5$ of which a refractive index is 2.39945 and of which a physical film thickness is 12.79 nm,
   a second layer made of $SiO_2$ of which a refractive index is 1.46037 and of which a physical film thickness is 36.78 nm,
   a third layer made of $Nb_2O_5$ of which a refractive index is 2.39945 and of which a physical film thickness is 34.56 nm,
   a fourth layer made of $SiO_2$ of which a refractive index is 1.46037 and of which a physical film thickness is 12.22 nm,
   a fifth layer made of $Nb_2O_5$ of which a refractive index is 2.39945 and of which a physical film thickness is 87.39 nm,
   a sixth layer made of $SiO_2$ of which a refractive index is 1.46037 and of which a physical film thickness is 20.11 nm,
   a seventh layer made of $Nb_2O_5$ of which a refractive index is 2.39945 and of which a physical film thickness is 24.69 nm,
   an eighth layer made of $SiO_2$ of which a refractive index is 1.46037 and of which a physical film thickness is 11.67 nm,
   a ninth layer made of $MgF_2$ of which a refractive index is 1.38559 and of which a physical film thickness is 98.66 nm, and
   an air layer, wherein the substrate is made of glass.

5. An optical element comprising the antireflection film claimed in claim 4.

6. An ophthalmology apparatus comprising the optical element claimed in claim 5.

7. An antireflection film provided on a substrate, the antireflection film comprising:
   as viewed from the substrate:
   a first layer made of $SiO_2$ of which a refractive index is 1.45441 and of which a physical film thickness is 31.86 nm,
   a second layer made of $Nb_2O_5$ of which a refractive index is 2.30466 and of which a physical film thickness is 17.9 nm,
   a third layer made of $SiO_2$ of which a refractive index is 1.45441 and of which a physical film thickness is 51.51 nm,
   a fourth layer made of $Nb_2O_5$ of which a refractive index is 2.30466 and of which a physical film thickness is 29.56 nm,
   a fifth layer made of $SiO_2$ of which a refractive index is 1.45441 and of which a physical film thickness is 24.34 nm,
   a sixth layer made of $Nb_2O_5$ of which a refractive index is 2.30466 and of which a physical film thickness is 150.84 nm,
   a seventh layer made of $SiO_2$ of which a refractive index is 1.45441 and of which a physical film thickness is 25.28 nm,
   an eighth layer made of $Nb_2O_5$ of which refractive index is 2.30466 and physical film thickness is 24.27 nm,
   a ninth layer made of $SiO_2$ of which a refractive index is 1.45441 and of which a physical film thickness is 14.11 nm,
   a tenth layer made of $MgF_2$ of which a refractive index is 1.37726 and of which a physical film thickness is 101.18 nm, and
   an air layer, wherein the substrate is made of glass.

8. An optical element comprising the antireflection film claimed in claim 7.

9. An ophthalmology apparatus comprising the optical element claimed in claim 8.

10. An antireflection film provided on a substrate, the antireflection film comprising:
    as viewed from the substrate:
    a first layer made of $Nb_2O_5$ of which a refractive index is 2.30113 and of which a physical film thickness is 7.11 nm,
    a second layer made of $SiO_2$ of which a refractive index is 1.45422 and of which a physical film thickness is 40.76 nm,
    a third layer made of $Nb_2O_5$ of which a refractive index is 2.30113 and of which a physical film thickness is 24.97 nm,
    a fourth layer made of $SiO_2$ of which a refractive index is 1.45422 and of which a physical film thickness is 21.63 nm,
    a fifth layer made of $Nb_2O_5$ of which a refractive index is 2.30113 and of which a physical film thickness is 145.89 nm,
    a sixth layer made of $SiO_2$ of which a refractive index is 1.45422 and of which a physical film thickness is 25.03 nm, a seventh layer made of $Nb_2O_5$ of which a refractive index is 2.30113 and of which a physical film thickness is 24.41 nm, an eighth layer made of $SiO_2$ of which a refractive index is 1.45422 and of which a physical film thickness is 11.83 nm, a ninth layer made of $MgF_2$ of which a refractive index is 1.37672 and of which a physical film thickness is 102.65 nm, and an air layer, wherein the substrate is made of glass.

11. An optical element comprising the antireflection film claimed in claim 10.

12. An ophthalmology apparatus comprising the optical element claimed in claim 11.

13. An antireflection film provided on a substrate, the antireflection film comprising:

as viewed from the substrate, a first layer made of $Nb_2O_5$ of which a refractive index is 2.39526 and of which a physical film thickness is 16.07 nm, a second layer made of $SiO_2$ of which a refractive index is 1.45998 and of which a physical film thickness is 24.33 nm, a third layer made of $Nb_2O_5$ of which a refractive index is 2.39526 and of which a physical film thickness is 41.6 nm, a fourth layer made of $SiO_2$ of which a refractive index is 1.45998 and of which a physical film thickness is 7.99 nm, a fifth layer made of $Nb_2O_5$ of which a refractive index is 2.39526 and of which a physical film thickness is 83.31 nm, a sixth layer made of $SiO_2$ of which a refractive index is 1.45998 and of which a physical film thickness is 21.46 nm, a seventh layer made of $Nb_2O_5$ of which a refractive index is 2.39526 and of which a physical film thickness is 24.55 nm, an eighth layer made of $SiO_2$ of which a refractive index is 1.45998 and of which a physical film thickness is 18.53 nm, a ninth layer made of $MgF_2$ of which a refractive index is 1.38531 and of which a physical film thickness is 78.51 nm, a tenth layer made of $SiO_2$ of which a refractive index is 1.45998 and of which a physical film thickness is 12.63 nm, and an air layer, wherein the substrate is made of glass.

14. An optical element comprising the antireflection film claimed in claim 13.

15. An ophthalmology apparatus comprising the optical element claimed in claim 14.

16. An antireflection film provided on a substrate, the antireflection film comprising:

as viewed from the substrate;

a first layer made of $SiO_2$ of which a refractive index is 1.45441 and of which a physical film thickness is 31.25 nm, a second layer made of $Nb_2O_5$ of which a refractive index is 2.30466 and of which a physical film thickness is 17.92 nm, a third layer made of $SiO_2$ of which a refractive index is 1.45441 and of which a physical film thickness is 51.19 nm, a fourth layer made of $Nb_2O_5$ of which a refractive index is 2.30466 and of which a physical film thickness is 29.53 nm, a fifth layer made of $SiO_2$ of which a refractive index is 1.45441 and of which a physical film thickness is 24.37 nm, a sixth layer made of $Nb_2O_5$ of which a refractive index is 2.30466 and of which a physical film thickness is 150.77 nm, a seventh layer made of $SiO_2$ of which a refractive index is 1.45441 and of which a physical film thickness is 25.2 nm, an eighth layer made of $Nb_2O_5$ of which a refractive index is 2.30466 and of which a physical film thickness is 24.42 nm, a ninth layer made of $SiO_2$ of which a refractive index is 1.45441 and of which a physical film thickness is 14.11 nm, a tenth layer made of $MgF_2$ of which a refractive index is 1.37726 and of which a physical film thickness is 86.73 nm, an eleventh layer made of $SiO_2$ of which a refractive index is 1.45441 and of which a physical film thickness is 11.68 nm, and an air layer, wherein the substrate is made of glass.

17. An optical element comprising the antireflection film claimed in claim 16.

18. An ophthalmology apparatus comprising the optical element claimed in claim 17.

* * * * *